United States Patent [19]

Lancini et al.

[11] Patent Number: 5,085,990
[45] Date of Patent: Feb. 4, 1992

[54] TEICOPLANIN-LIKE DERIVATIVES

[75] Inventors: Giancarlo Lancini, Pavia; Angelo Borghi, Milan; Piero Antonini, Arluno; Raffaele Palumbo, Brindis, all of Italy

[73] Assignee: Gruppo Lepetit S.P.A., Milano, Italy

[21] Appl. No.: 701,355

[22] Filed: May 10, 1991

Related U.S. Application Data

[63] Continuation of Ser. No. 214,231, Jul. 1, 1988, abandoned.

[30] Foreign Application Priority Data

Sep. 7, 1987 [GB] United Kingdom ................ 8720980

[51] Int. Cl.$^5$ .................... C12R 1/045; C12P 21/04
[52] U.S. Cl. ................ 435/71.3; 435/252.6; 435/827
[58] Field of Search .................. 435/71.3, 827, 252.6

[56] References Cited

U.S. PATENT DOCUMENTS

| | | | |
|---|---|---|---|
| 4,239,751 | 12/1980 | Coronelli et al. | 435/169 X |
| 4,328,316 | 5/1982 | Cavalleri et al. | 435/71.3 X |
| 4,542,018 | 9/1985 | Borghi et al. | 424/119 |
| 4,694,069 | 9/1987 | Dingerdissen et al. | 435/169 X |
| 4,778,846 | 10/1988 | Sitrin et al. | 530/417 X |

FOREIGN PATENT DOCUMENTS 259780 3/1988 European Pat. Off. ........... 435/71.3

Primary Examiner—Carolyn Elmore
Attorney, Agent, or Firm—J. Michael Dixon

[57] ABSTRACT

The present invention relates to new teicoplanin-like antibiotics differing from the parent compound in the length of the acyl group.

The compounds of the invention are obtained according to a microbiological process and possess an antimicrobiol activity mainly against gram positive bacteria.

6 Claims, 2 Drawing Sheets

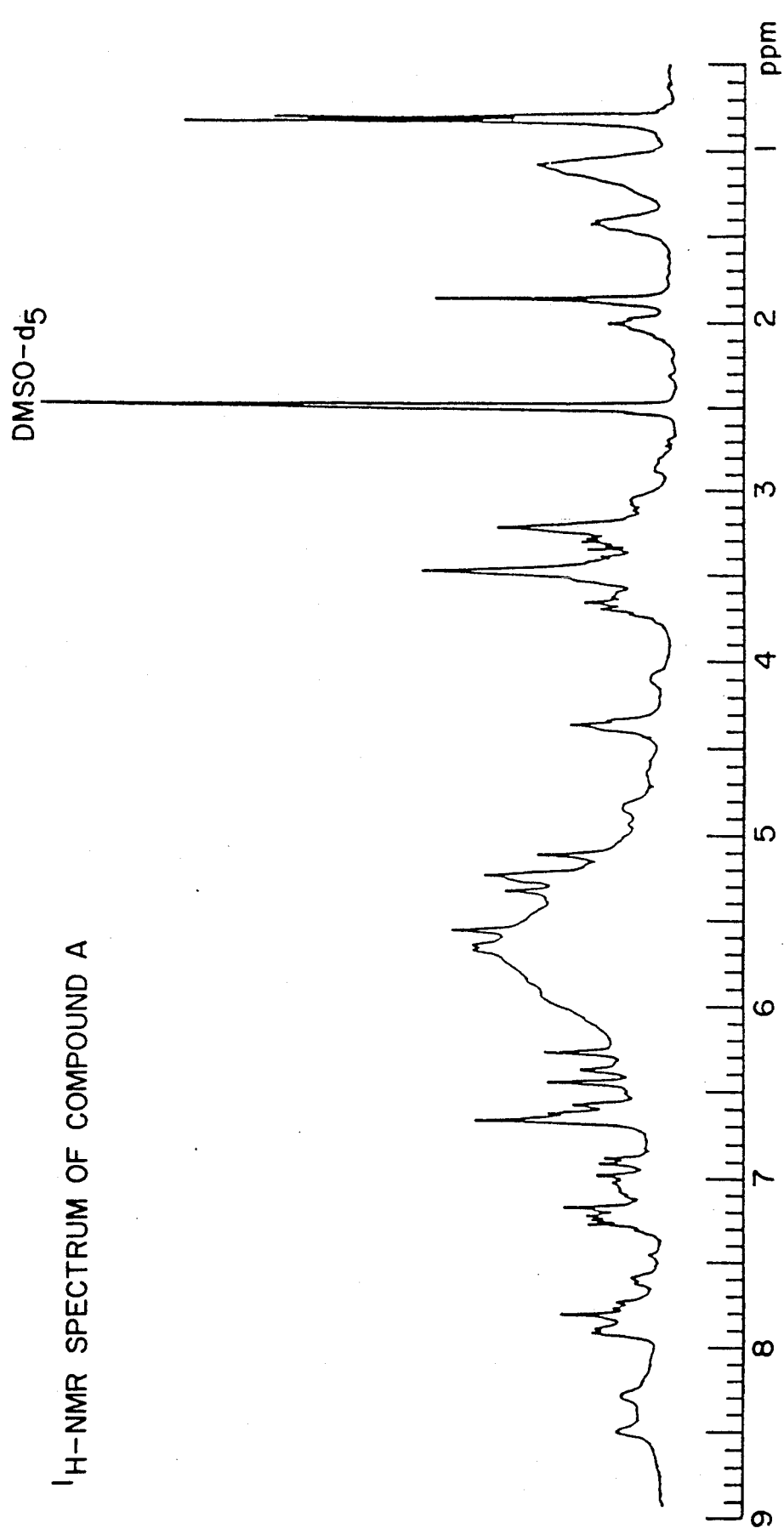

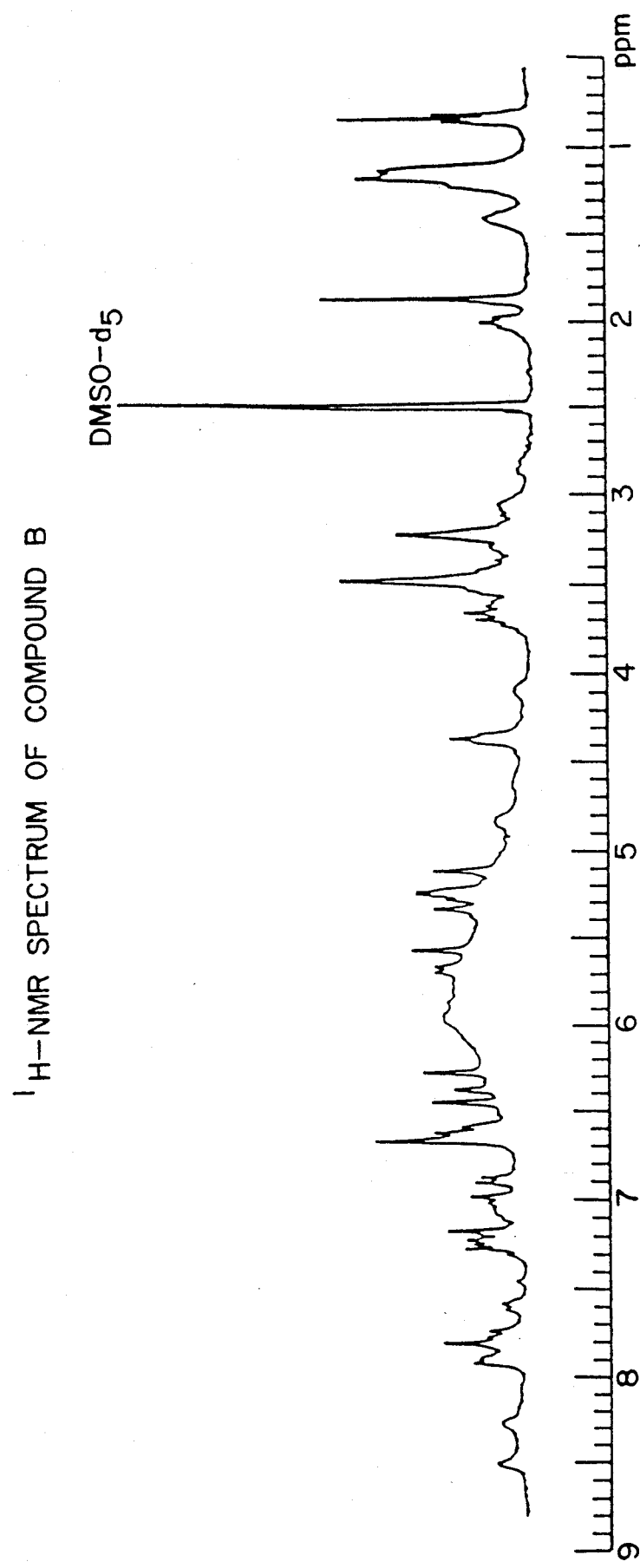

TEICOPLANIN-LIKE DERIVATIVES

This is a continuation of application Ser. No. 07/214,231, filed July 1, 1988, now abandoned.

The object of this invention are antibiotic teicoplanin-like derivatives of the formula

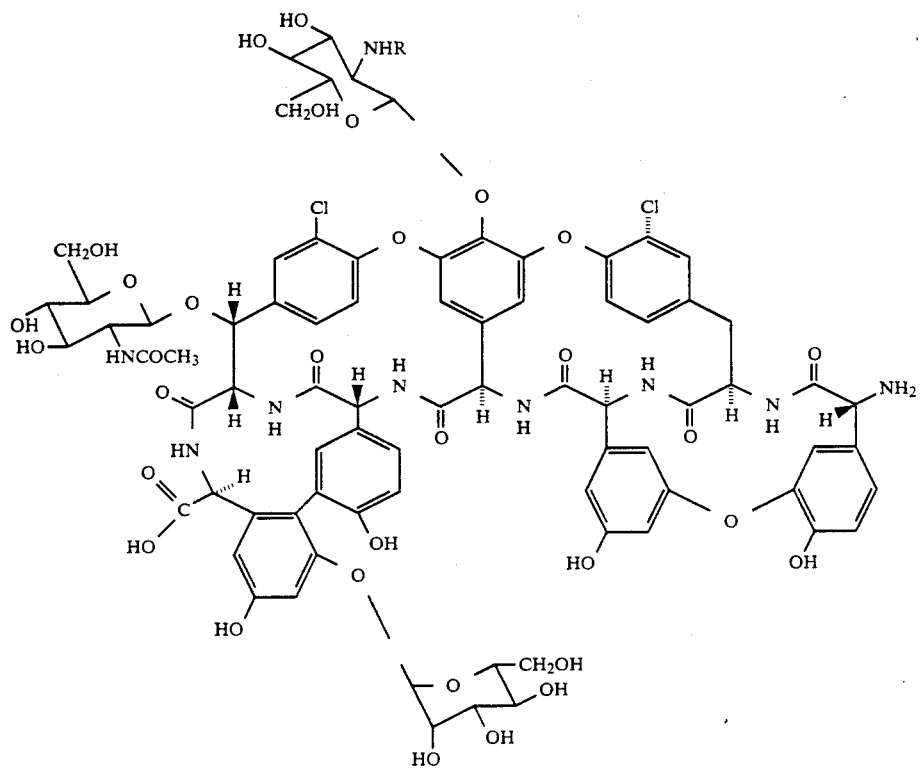

wherein:
R is 6-methyloctanoyl and n-nonanoyl,
their addition salts with acids and bases.

A further object of this invention is a process for the obtention of said antibiotic derivatives.

Teicoplanin is an antibiotic produced by cultivating the strain *Actinoplanes teichomyceticus* nov. sp. ATCC 31121 in a culture medium containing assimilable sources of carbon, nitrogen and inorganic salts.

The main product resulting from the above mentioned strain was a mixture of three main factors ($A_1$, $A_2$ and $A_3$) originally referred to as teichomycin (U.S. Pat. No. 4,239,751).

The more recent teicoplanin preparations obtained by purification of the product recovered from the fermentation broth and suitable for chemotherapeutic use in the treatment of infections caused by gram-positive organisms (H. H. Williams et al.: Journal of Hospital Infection (1986), 7 (Supplement A), 101-103) contain as the major component a complex of five structurally closely related substances which had been originally referred to, as whole, as teichomycin factor $A_2$. The above mentioned five closely related substances have been successively isolated and characterized as single components of the complex which is currently designated and referred to in the scientific papers and patent literature as "teicoplanin $A_2$" or "teicoplanin complex".

The five major components of teicoplanin complex (conventionally named: TA2-1, TA2-2, TA2-3, TA2-4 and TA2-5) may be represented by the above general formula (I) above wherein:
R respectively is:
TA2-1): N-(Z-4-decenoyl);
TA2-2): N-(8-methylnonanoyl);
TA2-3): N-decanoyl;
TA2-4): N-(8-methyldecanoyl);
TA2-5): N-(9-methyldecanoyl);

Their respective ratios in the teicoplanin complex can vary according to the fermentation conditions and the precursors added to the fermentation medium as described in the E.P.A. publication No. 204179.

The compounds of this invention can be obtained by fermentation of *Actinoplanes teichomyceticus* strains. In particular, a strain of *Actinoplanes teichomyceticus* which is characterized with our internal code No. A-184 has proved to be a suitable producer of the above mentioned teicoplanin-like derivatives. A sample of said strain has been deposited on July 21, 1987 at the ATCC (American Type Culture Collection, 12301 Parklawn Drive, Rockville, Md. 20852 U.S.A.) under the conditions established by the Budapest Treaty on the International Recognition of the Deposit of Microorganisms for the Purposes of Patent Procedure where it has been assigned the following ATCC number 53649.

The above strain identified by the ATCC No. 53649 is an artificial mutant of *Actinoplanes teichomyceticus* ATCC 31121, obtained by treatment with N-methyl-N'-nitro-N-nitrosoguanidine and selected on the basis of its ability to produce substantial amounts of teicoplanin-like antibiotics different from the five major components of the teicoplanin complex.

Mutant A-184 shows substantially the same morphological and physiological characteristics as the parent strain ATCC 31121 described in U.S. Pat. No. 4,239,751.

Is has now been found that small amounts of the antibiotics of this invention may be produced also by the parent strain *Actinoplanes teichomyceticus* ATCC 31121 under proper fermentation conditions, but the isolation of the small quantity of the invention compounds from the much larger amounts of the major components of teicoplanin complex produced by said microorganism is very laborious and is not practical for obtaining the desired compounds in a scale suitable for experimental purposes and practical utilization.

Also mutant A-184 produces a certain amount of the major components of teicoplanin complex together with the new compounds of this invention, but their relative ratio in the fermentation broth is much lower than that resulting from the parent strain. Therefore, the separation and recovery of the new compounds from the fermentation broth of mutant A-184 is much simpler and substantial amounts of the new teicoplanin-like derivatives can be obtained.

For the production of the compounds of this invention, the *Actinoplanes teichomyceticus* producing strain is fermented under aerobic conditions in an aqueous nutrient medium containing assimilable sources of carbon, nitrogen and inorganic salts.

Preferred carbon sources are glucose, mannose, galactose, starch, corn meal and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, manganese, magnesium, calcium, ammonium, chloride, iodide, carbonate, sulfate, phosphate, nitrate and the like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed. The producing-strain can be grown at temperatures between 20° and 40° C., preferably between 26° C. and 32° C.

During fermentation, the antibiotic production can be monitored by testing broth or mycelial extract samples for antibiotic activity for instance by bioassays or TLC or HPLC procedures.

Sensitive organisms to the antibiotics of this invention such as *Bacillus subtilis* and *S. aureus* can be used as test organisms. The bioassay is conveniently performed by the agar diffusion method on agar plates. Maximum production of antibiotic activity generally occurs between the second and the fifth day after inoculation.

The recovery of the antibiotic substances of this invention from the fermentation broths of the producing microorganism is conducted according to known per se techniques which include extraction with solvents, precipitation by adding non-solvents or by changing the pH of the solution, partition chromatography, reverse-phase partition chromatography, ion-exchange chromatography, affinity chromatography and the like.

A preferred procedure includes an affinity chromatography on immobilized D-Alanyl-D-Alanine followed by reverse-phase column chromatography.

Immobilized D-Alanyl-D-Alanine matrices suitable for the present recovery process are disclosed in European Patent Application Publication No. 122969. The preferred matrix in the present process is D-Alanyl-D-alanine coupled with a controlled pore cross-linked polydextrane.

The fermentation broth can be subjected to the affinity chromatography directly after filtration or after a preliminary purification procedure. This latter procedure includes making the whole fermentation mass basic, preferably between pH 9 and 11.5, in order to solubilize the antibiotic substance adsorbed on the mycelium and then filtering. The clear filtrate is brought to pH between 7 and 8 and then subjected to affinity chromatography on immobilized D-Alanyl-D-Alanine, either in column or batchwise.

Elution is performed at more basic pH values (preferably between 9.0 and 11.0) by means of an aqueous base. This aqueous base may be ammonia, a volatile amine, an alkali or alkali metal hydroxide or a basic buffered solution optionally in the presence of a polar organic solvent such as a polar water-miscible solvent. Fractions are collected, neutralized with an acid (either organic or inorganic, preferably, formic acid) and examined by HPLC to individuate those fractions which contain workable amounts of the compounds of this invention (the term "workable amount" is intended to mean that the amount of desired compound(s) contained in the eluted solution together with the major components of the teicoplanin complex is sufficient to permit its isolation in an appreciable quantity with the usual separation and purification techniques). Usually, the eluted fractions which contain at least 2% of one of the desired compounds on the total HPLC area relative to teicoplanin and teicoplanin-like products, are considered to contain a "workable amount" of the desired compound). Under the conditions of Example 2.2.3, the compound of formula I wherein R is 6-methyloctanoyl (compound A) has a retention time (RT) value of 19.93 minutes while the compound wherein R is n-nonanoyl (compound B) has an RT value of 20.96 minutes. As a reference, the RT value for TA2-2, under the same operational conditions is 24.71 minutes.

Those fractions which contain workable amounts of the desired compounds are pooled and concentrated by ultrafiltration and then lyophilized.

The crude product from lyophilization is dissolved in a polar aprotic organic solvent and then submitted in several portions to semi-preparative HPLC using a gradient mixture of a polar aprotic organic solvent and an aqueous ammonium salt as the mobile phase.

Examples of the polar aprotic organic solvent are ($C_1$-$C_4$)alkyl, lower alkyl amides or thio-amides, such as preferably dimethylformamide or diethylformamide.

Examples of ammonia salts are ammonia formate, ammonia acetate, methylammonium formate; ammonia formate being preferred.

In this case, the stationary phase is preferably a silanized silica gel, i.e. a silica gel functionalized with ($C_8$-$C_{22}$)alkyl groups.

A preferred mobile phase is represented by mixtures of 0.02M ammonium formate/acetonitrile 95:5 and 0.02M ammonium formate/acetonitrile 25:75.

From the eluates of each portion submitted to preparative HPLC the fractions containing Compound A and B respectively as the major products (HPLC analysis) are isolated and combined with those of the other portions. For instance, in a typical operation two solutions are obtained, the first of which contains about 80 percent of the 6-methyloctanoyl derivative with minor amounts (about 1.5 percent) of the n-nonanoyl compound while the second one contains about 90 percent of the n-nonanoyl compound with about 6 percent of 6-methyloctanoyl compound.

The two solutions are concentrated under vacuum, ultrafiltered and then lyophilized giving two solid products that are further purified by repeating the semi-preparative HPLC to yield the pure compounds of formula I whose characterization data are reported in the Examples.

As already said, the antibiotic substances of this invention possess acid and basic functions and can form salts according to conventional procedures.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like.

Representative examples of the bases are: alkali metal or alkaline-earth metal hydroxides such sodium, potassium, and calcium, hydroxide; ammonia and organic amines, i.e. aliphatic, alicyclic or aromatic amines such as methylamine, dimethylamine, trimethylamine, dimethylaniline and picoline.

The transformation of the free amino or non-salt compounds of the invention into the corresponding addition salts, and the reverse, i.e. the transformation of an addition salt of a compound of the invention into the non-salt form, are within the ordinary technical skill and are encompassed by the present invention.

For instance, a compound of the invention can be transformed into the corresponding acid or base addition-salt by dissolving the non-salt form in an aqueous solvent and adding a slight molar excess of the selected acid or base. The resulting solution or suspension is then lyophilized to recover the desired salt.

In case the final salt is insoluble in a solvent where the non-salt form is soluble it is recovered by filtration from the organic solution of the non-salt form after addition of the stoichiometric amount or a slight molar excess of the selected acid or base.

The non-salt form can be prepared from a corresponding acid or base salt dissolved in an aqueous solvent which is then neutralized to set free the non-salt form.

When following the neutralization desalting is necessary, a common desalting procedure may be employed.

For example, column chromatography on silanized silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the salt formation either with pharmaceutically acceptable acids (bases) or non-pharmaceutically acceptable acids (bases) may be used as a convenient purification technique. After formation and isolation, the salt form of an antibiotic of formula I above can be transformed into the corresponding non-salt or into a pharmaceutically acceptable salt.

The teicoplanin-like compounds of this invention are active against gram-positive bacteria which are responsible for many widely diffused infections, therefore they may be useful for preparing medicaments. Moreover, the compounds of this invention can be used as animal growth promoters, i.e. to increase the feed efficiency of meat or milk producing animals.

The antibacterial activity of the compounds of the invention can be demonstrated in vitro by means of standard dilution tests on different microorganism cultures.

Culture media and growth conditions for MIC (minimal inhibitory concentration) determinations were as follows: Isosensitest broth (Oxoid), 24 h, for staphylococci, *Strep. faecalis* and Gram-negative bacteria (*Escherichia coli*); Todd-Hewitt broth (Difco), 24 h for other streptococcal species; GC base broth (Difco)+1% Isovitalex (BBL), 48 h, $CO_2$-enriched atmosphere for *Neisseria gonorrhoeae;* Brain Heart broth (Difco)+1% Supplement C (Difco), 48 h for *Haemophilus influenzae;* Inocula were of about $10^4$–$10^5$ colony-forming units/ml for broth dilution MICs.

The minimal inhibitory concentrations (MIC, microgram/ml) of the above teicoplanin-like derivatives for some microorganisms are reported below in Table I.

TABLE I

| Strain | M.I.C. (microgram/ml) | |
|---|---|---|
| | Compound A | Compound B |
| *Staph. aureus* L165 | 0.5 | 0.5 |
| *Staph. aureus* ($10^6$ cfu/ml) | 2 | 1 |
| *Staph. aureus* (30% bovine serum) | 1 | 1 |
| *Staph. epidermidis* L147 ATCC 12228 (coagulase negative) | 0.5 | 0.25 |
| *Strep. pyogenes* L49 C203 | 0.063 | 0.063 |
| *Strep. pneumoniae* L44 UC41 | 0.125 | 0.125 |
| *Strep. faecalis* L149 ATCC 7080 | 0.5 | 0.25 |
| *Strep. mitis* L796 (clinical isolate) | 0.25 | 0.125 |
| *Neisseria gonorrhoeae* L997 ISM68/126 | 64 | 64 |
| *Haemophilus influenzae* L 970 type b ATCC 19418 | >128 | 128 |
| *Escherichia coli* L47 SKF 12140 | >128 | >128 |
| *Proteus vulgaris* L79 X19H ATCC881 | >128 | >128 |
| *Pseudomonas aeruginosa* L4 ATCC10145 | >128 | >128 |
| *Staph. haemolyticus* L602 (clinical isolate) | 32 | 16 |

For use as medicaments, the teicoplanin-like derivatives of this invention can be administered by different routes as free compounds or in the form of pharmaceutically acceptable salts. The parenteral administration is in general the preferred route.

For this purpose, a compound of the invention is preferably formulated into a pharmaceutical composition by administering it with a conventional carrier.

Compositions for injection are preferred and may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms.

In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pa., U.S.A., page 1614).

This could be specially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substances of the present invention and the physiologically acceptable salts thereof, are generally effective at a daily dosage of between about 1 and 20 mg of active ingredient per kilogram of patient body weight, optionally divided into 1 to 4 administrations per day.

Particularly desirable compositions are those prepared in dosage units containing from about 50 to about 2,000 mg per unit.

Sustained-action formulations can be prepared based on different mechanisms and methods, as known in the art.

A preferred method for preparing a sustained-action formulation containing the teicoplanin-like antibiotics of this invention, involves the use of a water insoluble form of the antibiotic suspended in an aqueous or oily medium.

For use as growth promoter, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and CO., S. Francisco, U.S.A., 1969 or "Livestock Feeds and Feeding" O and B books, Corvallis, Oreg., U.S.A., 1977) and are incorporated herein by reference.

BRIEF DESCRIPTION OF THE DRAWINGS

FIGS. 1 and 2 report the H-NMR spectra of compounds A and B, respectively.

EXAMPLES

EXAMPLE 1

Isolation of *Actinoplanes teichomyceticus* mutant strain A-184 (ATCC 53649)

A suspension of cells of the microbial strain *Actinoplanes teichomyceticus* ATCC 31121 in S/bis culture broth containing $10^8$–$10^9$ cells per ml is treated with N-methyl-N'-nitro-N-nitrosoguanidine (100 microg/ml) for 60 minutes in the presence of phosphate buffer (pH 7.0).

Then, samples of 0.1 ml of the suspension are re-suspended in 10 ml of fresh S/bis culture medium:

| | | |
|---|---|---|
| Glucose | 10 | g/l |
| Bacto Peptone Difco | 4 | g/l |
| Bacto Yeast Extract Difco | 4 | g/l |
| MgSO$_4$.7H$_2$O | 0.5 | g/l |
| KH$_2$PO$_4$ | 2 | g/l |
| K$_2$HPO$_4$ | 4 | g/l |
| pH = 7 after sterilization and plated on SM medium: | | |
| Glucose | 10 | g/l |
| Bacto Peptone Difco | 4 | g/l |
| Bacto Yeast Extract Difco | 4 | g/l |
| MgSO$_4$.7H$_2$O | 0.5 | g/l |
| KH$_2$PO$_4$ | 2 | g/l |
| K$_2$HPO$_4$ | 4 | g/l |
| Agar Difco | 20 | g/l |
| Sterilization: 15 min at 121° C. | | | at different dilutions (from $10^{-3}$ to $10^{-6}$ in a physiological solution) and incubated for thirteen days at 20° C.

Obtained colonies are randomly picked off and fermented in 500 ml Erlenmeyer flasks containing 100 ml of medium C:

| | | |
|---|---|---|
| Glucose$^{(a)}$ | 2 | g/l |
| Yeast extract | 5 | g/l |
| Asparagine | 1.5 | g/l |
| MgSO$_4$.7H$_2$O | 0.5 | g/l |
| CaCO$_3$ | 5 | g/l |
| NaCl | 0.1 | g/l |
| CaCl$_2$.2H$_2$O | 0.1 | g/l |
| Mineral supplement$^{(b)}$ | 1 | ml/l |
| pH = 6.9 after sterilization | | |
| $^{(a)}$glucose was sterilized separately | | |
| $^{(b)}$mineral supplement composition: | | |
| Boric acid | 0.50 | g/l |
| CuSO$_4$.5H$_2$O | 0.04 | g/l |
| KI | 0.10 | g/l |
| FeCl$_3$.6H$_2$O | 0.20 | g/l |
| MnSO$_4$.H$_2$O | 0.40 | g/l |
| FeSO$_4$.7H$_2$O | 0.40 | g/l |
| Ammonium molybdate | 0.20 | g/l |

The cultures broth are then analyzed by HPLC according to the procedure of Example 2, to identify those cultures producing teicoplanin-like compounds different from the five major components of the teicoplanin complex, in particular, those compounds showing RT values of 19.93 and 20.96 respectively.

Said cultures are selected, kept apart and frozen.

EXAMPLE 2

Preparation of compounds of formula I wherein R is 6-methyloctanoyl (compound A) and n-nonanoyl (compound B)

2.1 FERMENTATION

2.1.1 Culture Media

| S/bis: | | |
|---|---|---|
| Glucose | 10 | g/l |
| Bacto Peptone Difco | 4 | g/l |
| Bacto Yeast Extract Difco | 4 | g/l |
| $MgSO_4.7H_2O$ | 0.5 | g/l |
| $KH_2PO_4$ | 2 | g/l |
| $K_2HPO_4$ | 4 | g/l |
| pH = 7 after sterilization | | |
| Medium C: | | |
| Glucose[a] | 2 | g/l |
| Yeast extract | 5 | g/l |
| Asparagine | 1.5 | g/l |
| $MgSO_4.7H_2O$ | 0.5 | g/l |
| $CaCO_3$ | 5 | g/l |
| NaCl | 0.1 | g/l |
| $CaCl_2.2H_2O$ | 0.1 | g/l |
| Mineral supplement[b] | 1 | ml/l |
| pH = 6.9 after sterilization | | |
| [a]glucose was sterilized separately | | |
| [b]mineral supplement composition: | | |
| Boric acid | 0.50 | g/l |
| $CuSO_4.5H_2O$ | 0.04 | g/l |
| KI | 0.10 | g/l |
| $FeCl_3.6H_2O$ | 0.20 | g/l |
| $MnSO_4.H_2O$ | 0.40 | g/l |
| $FeSO_4.7H_2O$ | 0.40 | g/l |
| Ammonium molybdate | 0.20 | g/l |

2.1.2 Fermentation conditions

A frozen stock culture of the strain A-184 (2.5 ml) is used to inoculate a 500 ml Erlenmeyer flask containing 100 ml of vegetative medium (S/bis). The culture is incubated at 28° C. for 48 h on a shaker at 200 rpm and 5 cm throw.

This culture (400 ml) is used to inoculate a fermentor containing 4 l of production medium (Medium C). The jar is aerated with sterile air at a flow rate of 2 l/min and stirred at 900 rpm, while maintaining the temperature at 28° C.

2.2 ISOLATION

2.2.1 Recovery

The culture broth from four fermentors is harvested days after inoculation and after adjustment to pH 11 by addition of 2N NaOH is stirred for 15 minutes and then filtered under vacuum. The pH of the combined filtered broth (14 liters) is adjusted to 7.5 with HCl 2.5N. A suitable amount (200 ml) of Sepharose-acyl-D-alanyl-D-alanine affinity resin (A. Corti, G. Cassani - Synthesis and characterization of D-alanyl-D-alanine-agarose: a new bioselective adsorbent for affinity chromatography of glycopeptide antibiotics, Appl. Biochem. Biotec. 11, 101–109, 1985) is added and stirred overnight at 4° C. The resin is then separated from the exhausted broth and poured into a chromatographic column. The column is washed with 5-resin volume of Tris-HCl buffer (0.05M, pH 7.5) and then with the same volume of Tris base solution (0.05M). The column is then eluted with an aqueous solution of $NH_4OH$ (1 percent w/v) and 200 ml fractions are collected and examined by analytical HPLC (see under 2.2.3). Fractions containing the desired antibiotic substance (2 to 6) are selected and pooled and after neutralization with formic acid are concentrated by ultrafiltration (see under 2.2.2) to 70 ml. A crude of 2.53 g is then obtained by lyophilization. This crude product analyzed by HPLC shows presence of compounds A and B in amounts corresponding to about 4 percent and 12 percent respectively on the total HPLC area relative to teicoplanin and teicoplanin-like products. This crude product is then submitted to semi-preparative HPLC (see under 2.3.1).

2.2.2 ULTRAFILTRATION

The neutralized eluates are concentrated in a 142 mm Hi-Flux U-F Cell Millipore apparatus supporting a PCAC Pellicon ultrafiltration membrane with a nominal molecular weight limit (NMWL) of 1000 dalton.

2.2.3 Analytical HPLC

Apparatus: Hewlett Packard liquid chromatograph, mod. 1084 B; the UV detector is set at 254 nm.

Column: Erbasil C18 5 micrometer, 150×4.6 mm (Carlo Erba)

| Mobile phase: | A: 0.02 M $NaH_2PO_4$/$CH_3CN$ (95:5) | |
|---|---|---|
| | B: 0.02 M $NaH_2PO_4$/$CH_3CN$ (25:75) | |
| Gradient: | min | % B |
| | 0 | 8 |
| | 40 | 40 |
| | 45 | 55 |
| | 48 | 8 |
| | 50 | stop |

Flow rate: 1.5 ml/min
Column pressure: 200 atm
Injection volume: 20 microliter
Attenuation: 8
Chart speed: 0.5 cm/min
Standard: teicoplanin $A_2$ complex (A. Borghi et al.: The Journal of Antibiotics, Vol. 37, No. 6, pp 615–620, June 1984) dissolved in water to give a solution at the concentration of 1156.5 microgram/ml.

Under these conditions compound A shows a retention time (RT) of 19.93 minutes while compound B shows an RT of 20.96 minutes.

2.3 PURIFICATION AND CHARACTERIZATION

2.3.1 Semi-preparative HPLC

The crude resulting from lyophilization is subdivided in aliquots of 300 mg and dissolved in 1 ml of dimethylformamide to which 1 ml of a mixture of water/acetonitrile (1:1, v/v) is added. Each portion is then submitted to semi-preparative HPLC under the following conditions:

Apparatus: Hewlett Packard liquid chromatograph, mod. 1084 B; the UV detector was set at 254 nm Column: LiChrosorb RP-18 7 micrometer, 250×10 mm (Merck)

| Mobile phase: | A: 0.02 M $HCOONH_4$/$CH_3CN$ (95:5) | |
|---|---|---|
| | B: 0.02 M $HCOONH_4$/$CH_3CN$ (25:75) | |
| Gradient: | min | % B |
| | 0 | 25 |
| | 18 | 25 |
| | 22 | 65 |
| | 29 | 65 |
| | 30 | 25 |
| | 31 | stop |

Flow rate: 4 ml/min
Column pressure: 130 atm
Injection volume: 200 microliter
Attenuation: 1024
Chart speed: 0.5 cm/min Two fractions are isolated corresponding to the core of the peaks centered on RT value of 10.2 (fraction No. 1) and 12.4 minutes (fraction No. 2) respectively. The eluates from each injection are combined and checked by analytical HPLC (see under 2.2.3).

Two solutions having the following volumes and concentrations are obtained.

| Combined fractions No. | Volume (ml) | Conc. ($\mu$g/ml) | Total amount (mg) | % by HPLC Comp. A | Comp. B |
|---|---|---|---|---|---|
| 1 | 129 | 138.9 | 17.9 | 79.8 | 1.5 |
| 2 | 140 | 113.9 | 15.9 | 5.7 | 88.0 |

Most of the acetonitrile is eliminated under vacuum from the solutions 1 and 2 which are then concentrated by ultrafiltration and lyophilized giving the respective solid products.

The above described semi-preparative HPLC is repeated on the crude lyophilizates resulting from other three fermentation and recovery batches of the same size of that described under 2.1.2 and 2.2.1.

The solid products resulting from solutions 1 and 2 of each batch are then combined and further purified by resubmitting to semi-preparative HPLC operations under the same conditions described above. Yield 35.2 mg of compound A and 28.9 mg of compound B respectively, which are characterized by NMR spectroscopy and Fast Atom Bombardment Mass Spectrometry (FAB).

NMR and FAB spectra, clearly demonstrate that the structure of compound A is that of a teicoplanin having, as the side chain, a 6-methyloctanoyl moiety (formula I, R=6-methyloctanoyl), and the structure of compound B is that of a teicoplanin with an n-nonanoyl side chain (formula I, R=n-nonanoyl).

2.3.2 NMR spectroscopy

The instrument is a Bruker model AM-250 with an array processor, a magnet at 250 MHz and a computerized console Aspect 3000. The spectra is obtained in DMSO-$d_6$ solutions at 25° C. with tetramethylsilane as reference.

FIGS. 1 and 2 report the $^1$H-NMR spectra of compounds A and B respectively.

The attribution of the most significant peaks is given on the basis of comparison with the teicoplanin spectrum and on the basis of two dimensional spectroscopy, namely $^1$H homonuclear correlation spectroscopy. The spectra of compound A and compound B differ from those of teicoplanin $A_2$ complex components only in the aliphatic chain region. In fact, in compound A two methyl groups are found as shown by a triplet due to the CH$_2$—CH$_3$ moiety and a doublet due to the (CH)—CH$_3$ moiety nearly coincident at delta=0.8 ppm (J=6.4 Hz). In addition, there are four CH$_2$ groups in the chain, as deduced from the spectrum integral.

In compound B the terminal methyl group of the chain is shown by a triplet due to the (CH$_2$)—CH$_3$ moiety at delta=0.83 ppm (J=6.5 Hz). Seven CH$_2$ groups are present in the chain, as shown by the spectrum integral.

2.3.3 Fast Atom Bombardment-Mass Spectrometry

The instrument is a VG 70/250, using the mixture thioglycerol:glycerol (2:1, v/v) as a matrix. Bombardment gas: Xe; kinetic energy 6–8 keV; accelerating voltage 6 kV. Positive ion spectra are collected from m/z 600 to 2000.

The cationized molecular ions (MH$^+$ or MNa$^+$) and the adducts with the matrix determined by FAB-MAS indicate a molecular weight of 1849 (lowest isotope composition) for both compounds, in agreement with the NMR data.

We claim:

1. A process for preparing a teicoplanin-like compound of the formula

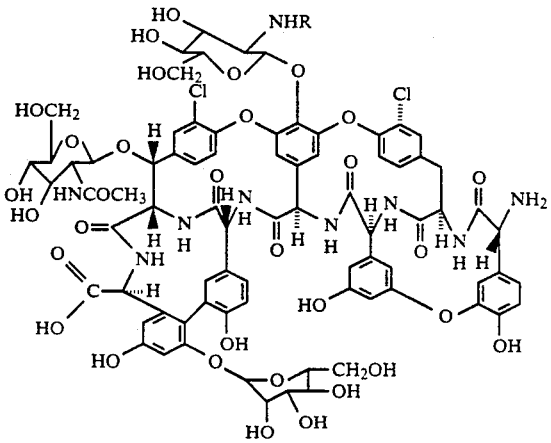

wherein:
R is 6-methyloctanoyl or n-nonanoyl, or an addition salt thereof with acids or bases, which comprises cultivating *Actinoplanes teichomyceticus* ATCC 53649 under aerobic conditions in an aqueous nutrient medium containing assimilable sources of carbon, nitrogen and inorganic salts, at a temperature between 20° C. and 40° C., separating and isolating said compound by means of chromatographic procedures.

2. A process according to claim 1 which comprises separating a crude from the filtered fermentation broth by contacting the filtered fermentation broth with an immobilized D-Alanyl-D-Alanine affinity matrix at a pH between 7 and 8, eluting the matrix with an aqueous base at a pH between 9 and 11, collecting those fractions which contain workable amounts of a teicoplanin-like compound of claim 1, pooling the fractions with homogeneous content, concentrating the pooled fractions by ultrafiltration and lyophilizing them.

3. A process according to claim 2 which comprises separating said teicoplanin-like compound from the other components of the crude by semi preparative HPLC using linear step gradient mixtures of aqueous ammonium formate and acetonitrile as the mobile phase.

4. A process according to claim 2 which comprises separating said leicoplanin-like compound from the outer components of the crude by semiammonium formate/acetonitrile 95:5 and 0.2M ammonium formate/acetonitrile 25:75.

5. *Acetinoplanes teichomyceticus* ATCC 53649.

6. A biologically pure culture of a strain of *Acetinoplanes teichomyceticus* ATCC 53649 which is capable of producing a compound of claim 1.

* * * * *